United States Patent
Rudischhauser et al.

(10) Patent No.: US 6,471,639 B2
(45) Date of Patent: Oct. 29, 2002

(54) ENDOSCOPE

(75) Inventors: Jürgen Rudischhauser, Tuttlingen (DE); Siegfried Höfig, Mühlheim (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/931,970

(22) Filed: Aug. 17, 2001

(65) Prior Publication Data

US 2001/0056222 A1 Dec. 27, 2001

Related U.S. Application Data

(63) Continuation of application No. PCT/EP99/01018, filed on Feb. 18, 1999.

(51) Int. Cl.$^7$ .................................................. A61B 1/12
(52) U.S. Cl. ...................... 600/128; 600/130; 600/138; 600/156
(58) Field of Search ................................. 600/104, 105, 600/121, 128, 130, 138, 153, 156, 135, 158

(56) References Cited

U.S. PATENT DOCUMENTS

| | | | |
|---|---|---|---|
| 4,867,138 A | 9/1989 | Kubota et al. | 128/6 |
| 5,048,508 A | 9/1991 | Storz | 128/4 |
| 5,257,617 A | * 11/1993 | Takahashi | 600/123 |

FOREIGN PATENT DOCUMENTS

WO    WO 94/11052    5/1994

OTHER PUBLICATIONS

R.Wolf, "Ambulanz–Dauerspul–Operations–Hysteroskop nach Grochmal".

Karl Storz Endoskope, "Instrument Set For The Treatment Of Bladder Stones".

* cited by examiner

Primary Examiner—John Mulcahy
(74) Attorney, Agent, or Firm—St. Onge Steward Johnston & Reens LLC

(57) ABSTRACT

An endoscope has an outer shaft, in which an optical channel receiving an optical system is arranged, wherein in the outer shaft, further, a channel for receiving a working element, at least one supply channel extending longitudinally for a medium and at least one discharge channel extending longitudinally for the discharge of a medium, the discharge being separated from the supply, are arranged. The optical channel and the at least one supply channel and/or the at least one discharge channel are configured as chambers of a profiled shaft, which is chambered in its cross section and received in the outer shaft.

16 Claims, 3 Drawing Sheets

ENDOSCOPE

CROSS REFERENCE TO PENDING APPLICATION

This application is a continuation of pending International Patent Application PCT/EP99/01018 filed on Feb. 18, 1999, which designates the United States.

BACKGROUND OF THE INVENTION

The invention relates to an endoscope, comprising an outer shaft, in which an optical channel receiving an optical system is arranged, wherein in the outer shaft, further, a working channel for receiving a working element, at least one supply channel extending longitudinally for a medium and at least one discharge channel extending longitudinally for discharging a medium separatedly from the supply, are arranged.

Such an endoscope is distributed as a combination instrument e.g. with instrument number 27092 AM-27093 B-27093 BI by the company Karl Storz GmbH & Co., Tuttlingen.

An endoscope of the type mentioned at the outset is used in minimally-invasive surgery for carrying out operations in human or animal bodies with simultaneous visual control.

The outer shaft of such an endoscope is, thus, designed in such a way that it can also receive a working element, e.g. dissecting forceps, which can be introduced from the proximal end through the outer shaft and which is held safely during the operation. The jaw parts of such a working element then project out of the distal open end of the outer shaft and can be actuated by means of a handle at the proximal end for carrying out the operation.

In order to be able to carry out an operation through an artificially created incision as small as possible in the body surface, the requirement on such an endoscope is such that the outer shaft has a diameter as small as possible. Since during an operation with the same endoscope several different working elements are used, which may differ in their diameters, the cross section remaining in the inner part of the outer shaft for the optical channel is limited by the maximal diameter of the largest working element used. To allow an optimal visual control of the operation with a great field of view and a high image quality, it is desirable, however, to use an optical system with a cross section as large as possible. It should be mentioned here that, in the sense of the present invention by an optical system every type of image transmission systems is understood, e.g. a relay lens system, glass fiber image guide or a video cable for a distally arranged video chip.

Furthermore, in such an endoscope is at least a supply channel for a medium, e.g. an irrigation liquid, and a discharge channel separated from the supply for discharging a medium, e.g. for discharging blood, tissue rests together with the irrigation liquid fed in. Such an arrangement allows a continuous irrigation and sucking off during the operation, so that the visual control through the optics is not affected by blood or loose tissue pieces during the operation.

In the known endoscope mentioned at the outset, first of all, an inner shaft is arranged within the outer shaft, wherein within the inner shaft the optical channel and the working channel are configured for receiving the working element. The inner shaft has in its cross section an approximately triangle shape, so that between the inner side of the outer shaft and the outer side of the inner shaft a discharge channel for discharging a medium and within the inner shaft between the optical channel and the working channel for the working element, a supply channel for a medium is formed. The optical channel, in which the optical system is arranged, is formed by another optical shaft. Furthermore, two other tubular shafts of also circular cross section receiving each a light supplying system in form of optical fibers are also connected to the optical shaft receiving the optical system.

It is to be considered as disadvantageous for this known endoscope that the cross section in the inner part of the outer shaft of the optical channel is reduced by the additional inner shaft, which is necessary in this embodiment, in order to form a supply channel and a discharge channel separated from same. Another restriction of the usable space within the outer shaft is caused by the fact that the working element is also received in the inner shaft. Due to this arrangement, for the optical channel and, thus, for the optical system, only a reduced cross section is available, which results in the disadvantage mentioned before of a smaller field of view and a lower image quality.

Another endoscope of this type is known from the DE firm brochure of company Richard Wolf GmbH, Knittlingen, "Ambulanz-Dauerspül-Operations-Hysteroskop nach Grochmal" ("Ambulance permanent irrigation operation hysteroscope according to Grochmal"). In this endoscope, four tubular shafts circular in cross-section are arranged within the outer shaft. A first tubular shaft forms the channel for receiving the working element, a second tubular shaft forms the supply channel, a third tubular shaft forms the discharge channel, and a fourth tubular shaft forms the optical channel. The space remaining between the individual tubular shafts and the inner side of the outer shaft is filled up with optical fibers, which are puttied with the outer shaft.

Also in this endoscope, the space available within the outer shaft is not optimally used, as an additional inner tubular shaft is provided for receiving the working element. This tubular shaft is, however, necessary to separate the working channel from the optical fibers, so that these are not damaged when the working element is introduced. Another disadvantage of this endoscope is that the outer shaft cannot be removed from the tubular shafts arranged inside due to the optical fibers between them.

U.S. Pat. No. 4,867,138 discloses an endoscope comprising a chambered profiled shaft received in the outer shaft, said profiled shaft contains an optical channel and at least one channel for receiving a light supplying illumination system. Between the outer shaft and the inner profiled shaft are configured two channels for supplying or discharging a medium. In one embodiment of this known endoscope the profiled shaft has a kidney-shaped outer contour. Outside of that profiled shaft there is a single supply channel for a medium. The supply channel is not separated from the discharge channel.

Further, WO 94/11052 discloses an endoscope having an inner profiled shaft in which supply and discharge channels are provided which are separated from the working channel, all the channels, however, are disposed within the profiled shaft, which completely-fills up the cross-section of the outer shaft.

It is therefore an object of the invention to improve an endoscope of the type mentioned at the outset in such a way that the arrangement of optical channel, working channel for receiving the working element, supply channel, discharge channel, and the channel for the illumination system guarantees an optimal exploitation of space of the interior of the outer shaft, so that the cross section available for the optical channel is as large as possible.

SUMMARY OF THE INVENTION

According to the invention, an endoscope is provided, comprising:

- an outer shaft;
- an optical channel for receiving an optical system, said optical channel being arranged in said outer shaft;
- at least one channel arranged in said outer shaft for receiving a light supplying illumination system;
- a profiled shaft arranged in said outer shaft and having an outer contour configured substantially in kidney-shaped fashion, said profiled shaft being chambered in cross-section, said optical channel and said at least one channel for said light supplying illumination system being configured as chambers of said profiled shaft;
- a working channel for receiving a working element, said working channel being arranged within said outer shaft and outside said profiled shaft and extending from a concave outer side of said profiled shaft until an opposite concave inner side of said outer shaft;
- at least one longitudinal supply channel for a liquid medium, and at least one longitudinal discharge channel for discharging a medium separatedly from said supply, wherein said profiled shaft has at least two further chambers which form at least one of said at least one supply channel and said at least one discharge channel.

For providing the optical channel and the at least one supply channel and/or the at least one discharge channel, in the endoscope of the invention, there is a profiled shaft chambered in cross-section and received in the outer shaft, which profiled shaft has a corresponding number of chambers for providing the individual channels. The optical system is here received in one of the chambers, while the at least one supply channel and/or the at least one discharge channel is formed by at least a further chamber of the profiled shaft. The channel for receiving the working element is then also formed between the profiled shaft and the inner side of the outer shaft. By the arrangement according to the invention of the optical channel and at least the supply channel or the discharge channel as chambers of the profiled shaft, a further inner shaft as in the prior art can be omitted, so that the cross section determined by the largest working element and being available for the optical channel can have the largest possible dimension. A profiled shaft has altogether the advantage of an optimal exploitation of space with respective maximally possible cross-sections of the chambers forming the individual channels, while an arrangement of individual cylindrical tubular shafts leads to empty spaces which cannot be used even with tightest packing. Another advantage of a profiled shaft is a higher flexural stiffness and, thus, a better protection of the endoscopy optics.

Further, the profiled shaft has at least another chamber for receiving a light supplying illumination system. It is here advantageous that not only the optical system, but also the light supplying illumination system, e.g. in form of optical fibers, can also be configured in the profiled shaft with a cross section as large as possible, whereby a bright illumination of the operation area is achieved. Whereas for the endoscope known from the DE firm brochure of Richard Wolf GmbH, Knittlingen, the optical fibers fill the space remaining between the outer shaft and the inner shafts, whereby the whole arrangement of outer shaft, optical fibers and inner shafts cannot be disassembled, it is also achieved by the present embodiment advantageously that the arrangement of outer shaft and profiled shaft with the optical fibers integrated therein can be configured in such a way that it can be disassembled.

According to another aspect of the invention, the outer contour of the profiled shaft is configured substantially in kidney-shaped fashion, wherein a concave outer side of the profiled shaft with an opposite inner side of the outer shaft forms the working channel for the working element. This measure has now the particular advantage that, for forming the working channel for receiving the working element, another tubular shaft as provided in the prior art can be omitted, so that the available diameter within the outer shaft is enlarged by the double wall thickness of such an additional tubular shaft. Between the concave outer side of the profiled shaft and the opposite inner side of the outer shaft, the working element is, apart from that, safely guided when being inserted into the outer shaft and safely held during the operation.

In a preferred embodiment, a convex outer side of the profiled shaft, which is in contact with an inner wall portion of the outer shaft, extends beyond the half of the inner circumference of the outer shaft.

This measure has the advantage that the profiled shaft in the outer shaft is fixed in the outer shaft without additional fixing measures, even if the working element is not yet inserted into the outer shaft. As no further fixing of the profiled shaft in the outer shaft is necessary, this offers the advantageous possibility to configure the outer shaft removable from the profiled shaft, which then allows an easier and more thorough cleaning of the endoscope.

In another preferred embodiment, some of the chambers are not circular in their cross sections.

This measure has the advantage that the profiled shaft can be configured with a particularly high flexural stiffness, whereby in particular the optical system in the optical channel is protected against fracture. As the optical channel is usually circular in cross section because of the optical system received therein, the chamber forming the supply channel or the discharge channel can be configured in not circular fashion. For the endoscope known from the DE firm brochure of company Richard Wolf GmbH, Knittlingen, in which the individual channels are formed by cylindrical thin shafts, the flexural stiffness is reduced with difference to the embodiment of the invention.

In a further preferred embodiment, the profiled shaft is removable out of the outer shaft.

It is here advantageous, on the one hand, that the cleanability of the endoscope is improved, on the other hand, several outer shafts can be held at the disposal, which can be exchanged against each other if the same profiled shaft is used. By using different outer shafts, working channels of different sizes for receiving the working element can be realized, if necessary.

In another preferred embodiment, a diameter of the chamber forming the optical channel and a diameter of the working channel for the working element are arranged on the same diameter of the outer shaft.

In this arrangement and embodiment of the profiled shaft, the chamber forming the optical channel can be advantageously configured with an outer diameter, which equals approximately the difference between the inner diameter of the outer shaft and the outer diameter of the working element, whereby an optimal exploitation of the cross section maximally available for the optical channel is achieved.

In another preferred embodiment, the profiled shaft has such an outer dimension that between the working element, the inner side of the outer shaft and the profiled shaft at least a further discharge channel and/or a supply channel for a medium is arranged.

In this embodiment, the profiled shaft can have, for example, a chamber that forms the supply channel for a medium, while the free space remaining between the working element, the inner side of the outer shaft and the profiled shaft serves then as a discharge channel for a medium. In that way, advantageously the whole inner cross section of the outer shaft is functionally used.

In another preferred embodiment, the profiled shaft has, in its cross section, five chambers.

In this configuration of the profiled shaft, for example, one chamber for forming the optical channel with a cross section as large as possible can be provided, while the other four chambers can form e.g. the supply channel, the discharge channel and one or two channels for the light supplying illumination system.

In another preferred embodiment, the profiled shaft is configured in one piece.

It is here advantageous that the profiled shaft can be manufactured in a single working step with the shape desired, whereby the manufacture and the cost expenditure of the profiled shaft is advantageously reduced.

Alternatively, it can also be preferred, however, if the profiled shaft is assembled of a number of individual profiles corresponding to the number of chambers.

This configuration of the profiled shaft is also advantageous, as the profiled shaft, in that way, can be assembled to the arrangement desired of the individual chambers, in the type of a modular system.

Further advantages can be taken from the following description and the attached drawings.

It is to be understood that the features mentioned above and those yet to be explained below can be used not only in the respective combinations indicated, but also in other combinations or in isolation, without leaving the scope of the present invention.

BRIEF DESCRIPTION OF THE DRAWINGS

Embodiments of the invention is shown in the drawings and will be explained in more detail in the description below. In the drawings.

DETAILED DESCRIPTION OF PREFERRED EMBODIMENTS

Figure 1:
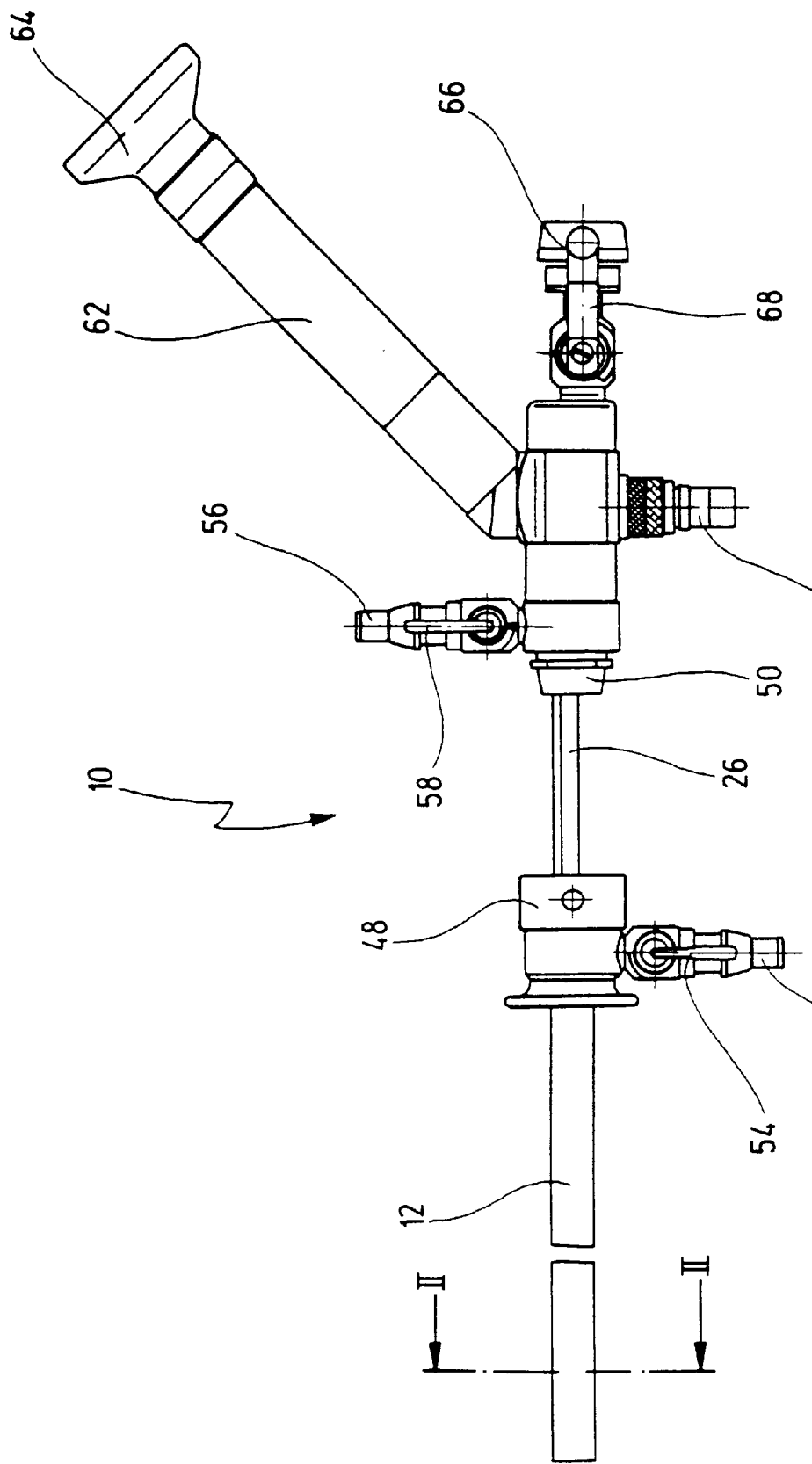
FIG. 1 shows a side view of an endoscope in total.

In FIG. 1, an endoscope is shown, which is labeled with the general reference numeral 10. Endoscope 10 serves in minimally-invasive surgery for carrying out operations in human or animal bodies with simultaneous sight control.

Endoscope 10 has an elongated outer shaft 12. According to FIG. 2, which shows a cross section along line II—II through endoscope 10 in FIG. 1 in an enlarged scale, an optical channel 14 is arranged in outer shaft 12, which channel receives a schematically represented optical system 16, which comprises e.g. a relay lens system.

In outer shaft 12, there is further a working channel 18 for receiving a schematically shown working element 20. Working element 20 is e.g. a dissecting forceps, by means of which the operation is performed.

Furthermore, in outer shaft 12, there is a longitudinally extending supply channel 22 for a medium, e.g. for an irrigation liquid, which is fed into the operation area through supply channel 22. Apart from that, there is, in outer shaft 12, a discharge channel 24 for a medium, through which e.g. the irrigation liquid can be sucked off together with blood or tissue rests, so that continuous irrigating and sucking off during the operation is possible.

Optical channel 14 as well as supply channel 22 for a medium are configured as chambers of a profiled shaft 26, which is received in outer shaft 18.

A first intermediate chamber, which forms optical channel 14, is configured circular in its cross section. Two chambers 30 and 32 adjoining intermediate chamber 28 form together supply channel 22 for supplying a medium. Chambers 30 and 32 are configured not circular in cross section.

Profiled shaft 26 has two further outer chambers 34 and 36, in which each a light supplying illumination system 38 is received, which is formed by individual optical fibers 40. Optical fibers 40 fill up chamber 34 and/or chamber 36 completely.

Figure 2:
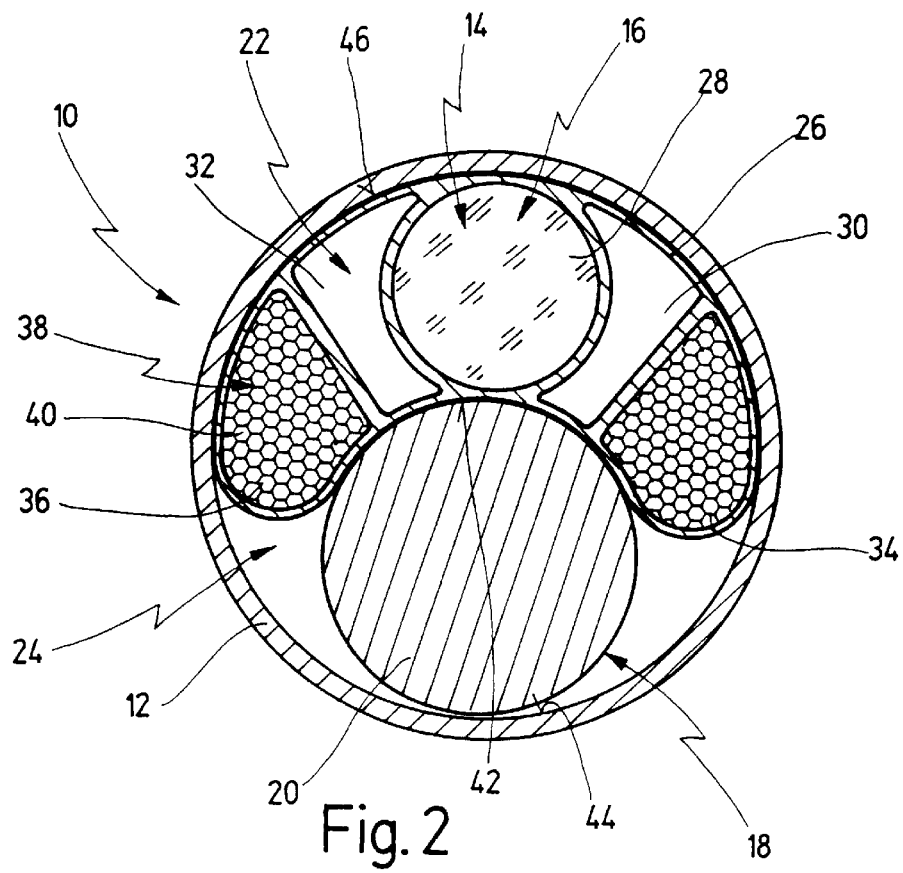
FIG. 2 shows a section through the endoscope along line II—II in FIG. 1 in an enlarged scale.

As can be seen from FIG. 2, an outer contour of profiled shaft 26 is configured approximately in kidney-shaped fashion, wherein a concave outer side 42 of profiled shaft 26 with an opposite inner side 44 of outer shaft 12 forms working channel 18 for receiving working element 20. Between concave outer side 42 and inner side 44 opposite to same, working element 20 is guided and held safely. For forming working channel 18 in order to receive working element 20, thus, no further shaft is necessary.

Chamber 28 forming optical channel 14 is arranged in such a way in profiled shaft 26 that a diameter of chamber 28 and a diameter of channel 18 for working element 20 are arranged on the same diameter of outer shaft 12. In that way, the largest diameter possible is achieved for optical channel 14, when the cross section of working element 20 is predetermined, so that optical system 16 can be configured with maximal diameter, whereby, again, the image quality of visual observation of the operation is ameliorated.

Discharge channel 24 is formed by the remaining space between profiled shaft 26, more precisely, between chambers 34 and 36, and working element 20.

Profiled shaft 26 has, due to its shape, a high flexural stiffness.

A convex outer side 46 of profiled shaft 26 is in contact with outer shaft 12 and extends beyond the half of the inner circumference of outer shaft 12. It is, thus, achieved that without additional fixing measures, profiled shaft 26 is fixed in outer shaft 12, even if working element 20 is not yet inserted into outer channel 18.

Again with reference to FIG. 1, profiled shaft 26 can be removed from outer shaft 12, or outer shaft 12 can be withdrawn from profiled shaft 26. In FIG. 1, outer shaft 12 is shown in a position slightly shifted with respect to profiled shaft 26. In operation of endoscope 10, outer shaft 12 is, however, firmly connected via a bayonet coupling consisting of a mount 48 connected to outer shaft 12 and a mount 50 connected to profiled shaft 26.

At outer shaft 12, further, a connection 52 is arranged for connecting a suction line not shown, which is in connection with a suction device. Connection 52 communicates with discharge channel 24. A shut-off valve 54 serves for opening and shutting off discharge channel 24.

At the proximal end of profiled shaft 26, further, a connection 56 is arranged for connecting a line (not shown) for the supply of a medium, e.g. an irrigation liquid line. Connection 56 communicates with supply channel 22, i.e.

more precisely, with chambers 30 and 32 of profiled shaft 26. Connection 56 also a has shut-off valve 58.

An optical fiber connection 60 serves for connecting a light supplying optical fiber cable in order to couple in light from an external light source into optical fibers 40 in chambers 34 and 36 of profiled shaft 26.

An eyepiece tube 62 with an eyepiece cup 64 serves for watching the operation area imaged through optical system 16.

Finally, at the proximal end of endoscope 10, in extension of working channel 18, a coupling 66 for inserting working element 20 not shown in FIG. 1 is arranged, wherein working element 20 can be fixed after inserting by means of a locking device 68.

Profiled shaft 26 is altogether configured in one piece. Profiled shaft 26, however, can also be made up of individual profiles, each individual profile forming one of chambers 28 through 36.

Figure 3:
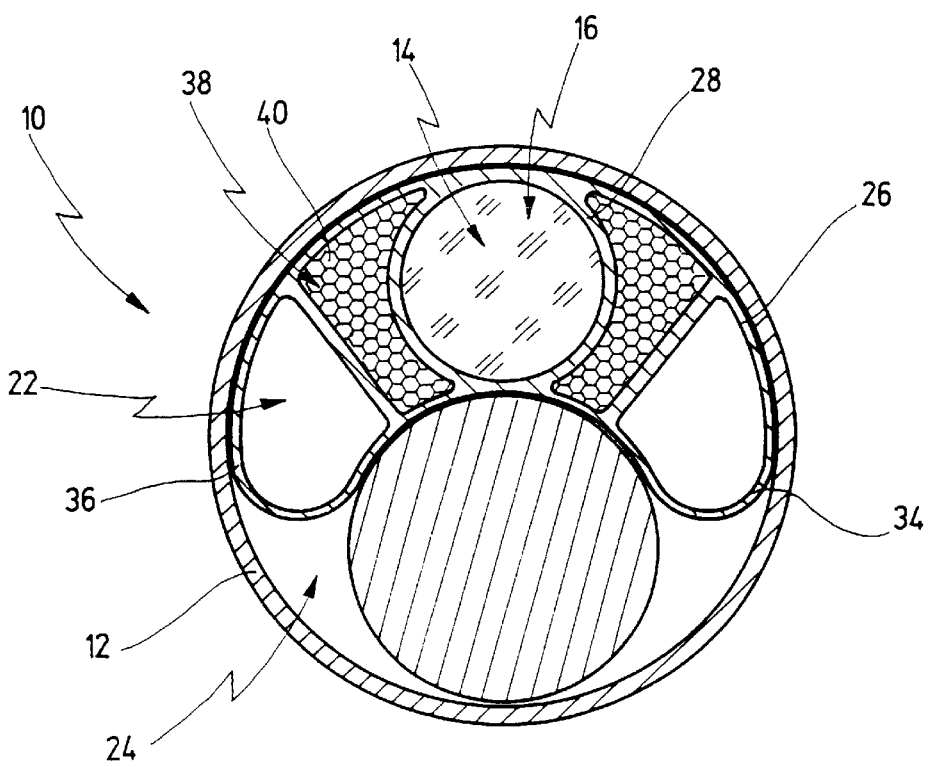
FIG. 3 shows a cross section corresponding to FIG. 2 according to another embodiment.

In FIG. 3, a slightly modified embodiment is shown, in which light supplying illumination system 38 is received in chambers 30 and 32 adjacent to chamber 28, which, again, forms optical channel 14, while chambers 34 and 36 form supply channel 22 for a medium. The cross section profile of profiled shaft 26 is identical in the embodiment shown in FIG. 3 with the embodiment shown in FIG. 2.

Figure 4:
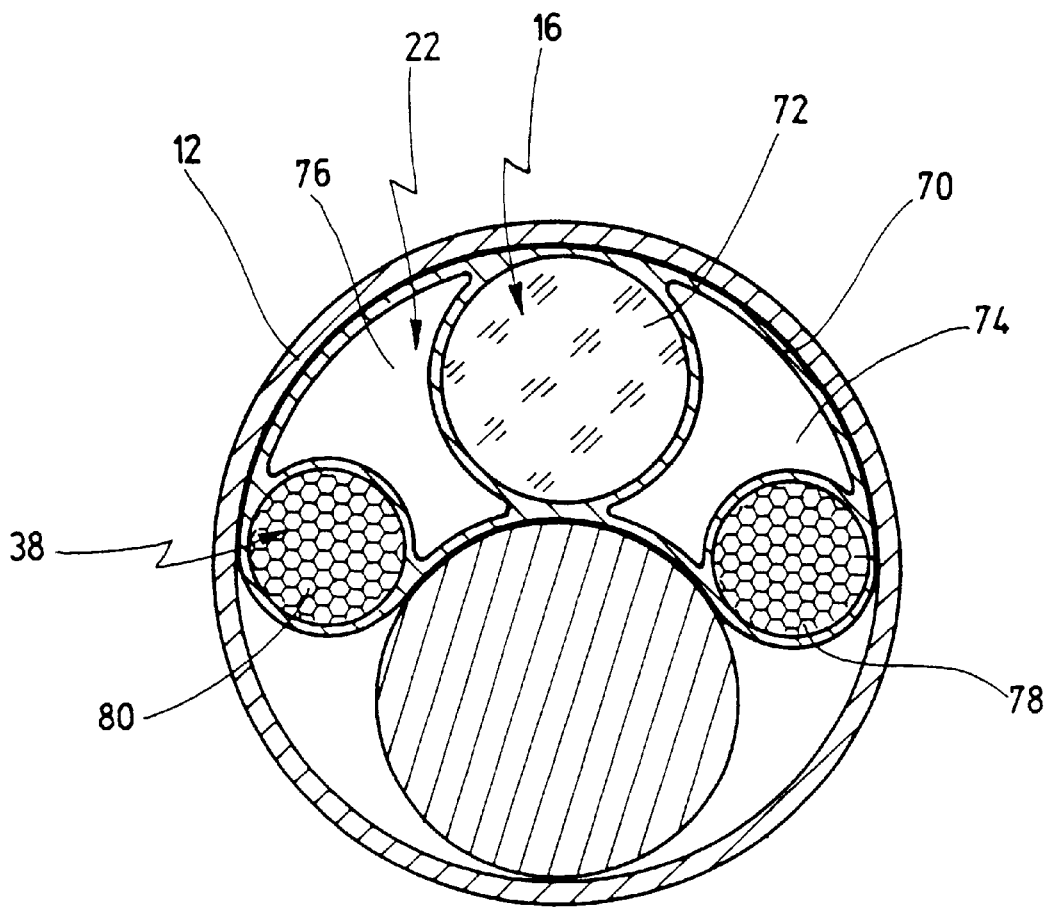
FIG. 4 shows a cross section corresponding to FIG. 2 according to still another embodiment.

In FIG. 4, another embodiment of an endoscope is shown, which differs from the previous embodiments by a profiled shaft 70, which indeed has five chambers 72 through 80, which, however, have a different cross section profile in comparison with the previous embodiments. In that way, chambers 78 and 80, which receive light supplying illumination system 38, have a circular cross section, just as chamber 72, which receives optical system 16.

Chambers 74 and 76 form together supply channel 22.

While the embodiments previously described are preferred, it is to be understood that e.g. in FIG. 2 supply channel 22 can only be formed by chamber 32 of profiled shaft 26, while chamber 30 of profiled shaft 26 can also form discharge channel 24 or another additional discharge channel. Apart from that, it is possible that chamber 32 can form the supply channel for a liquid and chamber 30 can form the supply channel for a gas.

It is further to be understood that the cross section profiles of the individual chambers of profiled shaft 26 and/or profiled shaft 70 can be adjusted to the respective requirements in the discretion of those skilled in the art.

What is claimed is:

1. An endoscope, comprising:
   an outer shaft;
   an optical channel for receiving an optical system, said optical channel being arranged in said outer shaft;
   at least one channel arranged in said outer shaft for receiving a light supplying illumination system;
   a profiled shaft arranged in said outer shaft and having an outer contour configured substantially in kidney-shaped fashion, said profiled shaft being chambered in cross-section, said optical channel and said at least one channel for said light supplying illumination system being configured as chambers of said profiled shaft;
   a working channel for receiving a working element, said working channel being arranged within said outer shaft and outside said profiled shaft and extending from a concave outer side of said profiled shaft until an opposite concave inner side of said outer shaft;
   at least one longitudinal supply channel for a liquid medium, and at least one longitudinal discharge channel for discharging a medium separatedly from said supply, wherein said profiled shaft has at least two further chambers which form at least one of said at least one supply channel and said at least one discharge channel.

2. The endoscope of claim 1, wherein some of said chambers have not circular cross-sections.

3. The endoscope of claim 1, wherein said profiled shaft is removable out of said outer shaft.

4. The endoscope of claim 1, wherein said optical channel and said working channel have a circular cross-section, and a diameter of said chamber forming said optical channel and a diameter of said working channel for said working element are arranged on a second diameter of said outer shaft.

5. The endoscope of claim 1, wherein said profiled shaft has such an outer dimension that between said working channel, the inner side of said outer shaft and said profiled shaft at least one further discharge channel and/or a supply channel for a medium is arranged.

6. The endoscope of claim 1, wherein said profiled shaft has five chambers in its cross-section, wherein said optical channel is formed by an intermediate chamber, and said supply channel and/or said discharge channel and said channel for said light supplying illumination system is formed by chambers arranged on both sides of said optical channel.

7. The endoscope of claim 1, wherein said profiled shaft is configured in one piece.

8. The endoscope of claim 1, wherein said profiled shaft is assembled of a number of individual profiles corresponding to the number of chambers.

9. An endoscope, comprising:
   an outer shaft having a circular cross-section;
   an optical channel for receiving an optical system, said optical channel being arranged in said outer shaft;
   at least one channel arranged in said outer shaft for receiving a light supplying illumination system;
   a profiled shaft arranged in said outer shaft and having an outer contour configured substantially in kidney-shaped fashion, said profiled shaft being chambered in cross-section, said optical channel and said at least one channel for said light supplying illumination system being configured as chambers of said profiled shaft, wherein a convex outer side of said profiled shaft, which is in contact with said outer shaft, extends beyond the half of the inner circumference of said outer shaft;
   a working channel for receiving a working element, said working channel being arranged within said otter shaft and outside said profiled shaft and extending from a concave outer side of said profiled shaft until an opposite concave inner side of said outer shaft;
   at least one longitudinal supply channel for a liquid medium, and at least one longitudinal discharge channel for discharging a medium separatedly from said supply, wherein said profiled shaft has at least two further chambers which form at least one of said at least one supply channel and said at least one discharge channel.

10. The endoscope of claim 9, where in some of said chambers have not circular cross-sections.

11. The endoscope of claim 9, wherein said profiled shaft is removable out of said outer shaft.

12. The endoscope of claim 9, wherein said optical channel and said working channel have a circular cross-section, and a diameter of said chamber forming said optical channel and a diameter of said working channel for said working element are arranged on a second diameter of said outer shaft.

13. The endoscope of claim 9, wherein said profiled shaft has such an outer dimension that between said working channel, the inner side of said outer shaft and said profiled shaft at least one further discharge channel and/or a supply channel for a medium is arranged.

14. The endoscope of claim 9, wherein said profiled shaft has five chambers in its cross section, wherein said optical channel is formed by an intermediate chamber, and said supply channel and/or said discharge channel and said channel for said light supplying illumination system is formed by chambers arranged on both sides of said optical channel.

15. The endoscope of claim 9, wherein said profiled shaft is configured in one piece.

16. The endoscope of claim 9, wherein said profiled shaft is assembled of a number of individual profiles corresponding to the number of chambers.

* * * * *